(12) United States Patent
Eriten et al.

(10) Patent No.: US 12,710,399 B2
(45) Date of Patent: Aug. 18, 2026

(54) METHOD AND APPARATUS FOR EVALUATING SOFT MATERIAL PROPERTIES USING NONLINEAR VIBRATIONS

(71) Applicant: Wisconsin Alumni Research Foundation, Madison, WI (US)

(72) Inventors: Melih Eriten, Madison, WI (US); Karthik Yerrapragada, Madison, WI (US); Haocheng Yang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 343 days.

(21) Appl. No.: 18/532,481

(22) Filed: Dec. 7, 2023

(65) Prior Publication Data

US 2025/0189493 A1 Jun. 12, 2025

(51) Int. Cl.

| | |
|---|---|
| ***G01N 29/24*** | (2006.01) |
| ***G01B 17/02*** | (2006.01) |
| ***G01N 29/04*** | (2006.01) |
| *A61B 8/00* | (2006.01) |

(52) U.S. Cl.

CPC ......... *G01N 29/2418* (2013.01); *G01B 17/02* (2013.01); *G01N 29/04* (2013.01); *A61B 8/485* (2013.01); *G01N 2291/023* (2013.01); *G01N 2291/02827* (2013.01); *G01N 2291/02854* (2013.01)

(58) Field of Classification Search

CPC ............... G01N 29/2418; G01N 29/04; G01N 2291/023; G01N 2291/02827; G01N 2291/02854; G01B 17/02; A61B 8/485

See application file for complete search history.

(56) References Cited

U.S. PATENT DOCUMENTS

| | | | | |
|---|---|---|---|---|
| 6,006,593 | A * | 12/1999 | Yamanaka | G01Q 60/32 977/851 |
| 6,314,322 | B1 * | 11/2001 | Rosenberg | A61N 1/36514 607/9 |
| 2013/0174666 | A1 * | 7/2013 | Hadj Henni | G01N 11/16 73/800 |

FOREIGN PATENT DOCUMENTS

| | | |
|---|---|---|
| CA | 2922275 A1 | 3/2015 |

OTHER PUBLICATIONS

Chen et al.; "Large-amplitude vibration of an initially stressed thick circular plate." AIAA journal vol. 21, No. 9 (Sep. 1983): pp. 1317-1324. US.

Boz et al.; "Nonlinear system identification of soft materials based on Hilbert transform." Journal of Sound and Vibration 447 (2019 published by Elsevier); pp. 1-36.

Darger et al.; "In situ mechanical characterization of multilayer soft tissue using ultrasound imaging." IEEE Transactions on Biomedical Engineering 64, No. 11 (2016): pp. 2595-2606. US.

* cited by examiner

*Primary Examiner* — Tarun Sinha

(74) *Attorney, Agent, or Firm* — Boyle Fredrickson, S.C.

(57) ABSTRACT

An apparatus for measuring elastic properties of materials excites the material into nonlinear vibration to reveal, in a free and forced vibration signals, information about Young's modulus, internal stress, and material thickness obtained from nonlinear and linear vibration information.

19 Claims, 3 Drawing Sheets

METHOD AND APPARATUS FOR EVALUATING SOFT MATERIAL PROPERTIES USING NONLINEAR VIBRATIONS

STATEMENT REGARDING FEDERALLY SPONSORED RESEARCH OR DEVELOPMENT

This invention was made with government support under 2200353 awarded by the National Science Foundation. The government has certain rights in the invention.

CROSS REFERENCE TO RELATED APPLICATION

Background of the Invention

The present invention relates generally to an apparatus for measuring the properties of soft, elastic materials and in particular to an apparatus that utilizes nonlinear vibration to better characterize those materials.

Soft materials such as hydrogels, soft biological tissues, elastomers, and foams have a wide range of applications in the fields of robotics and sensing, in biomedical, pharmaceutical and agrifood industries. Multiphasic soft materials are a subset of soft materials that contain one or more phases in addition to a solid scaffold, for example, liquid-imbibed gels and foams as well as soft tissues formed by fibrous solid network swollen with physiological fluids and ions, etc.

Characterizing the mechanical properties of multiphasic materials can be important in many applications. In the food industry, for instance, such characterization can help evaluate dehydration and aid in the processing of vegetables and fruits. In the biomedical industry, characterizing the mechanical properties of multiphasic materials can help distinguish healthy tissue from cancerous tissues as well as evaluate the malignancy of cancerous tissues. Real-time monitoring of the mechanical properties of multiphasic materials can also help to understand and predict the growth and fate of the engineered tissues. In robotic and sensing applications, such monitoring can be used to assess degradation of elastomers over time or to investigate the operation of multiphasic materials having magnetic or ionic phases for adaptive reshaping of actuators or the production of flexible electronics.

Transport and chemical reactions can alter the constituents of multiphasic materials, which can then cause their properties to change significantly in response to their environment. For example, the elastic modulus and internal stresses in those materials may vary over orders of magnitude with temperature, pH, humidity, osmolarity, and electric and magnetic fields. Accordingly, it would be desirable to have a method of simply and rapidly obtaining measurements of such materials over time.

One method of making such elastic measurements characterizes the materials based on vibration, for example, as described in Canadian patent 2922275, hereby incorporated by reference. This patent describes a vibration-based testing system that may deduce Young's modulus of a test material.

SUMMARY OF THE INVENTION

The present invention inventors have recognized that additional information beyond Young's modulus can be obtained through vibration measurements by inducing vibrations in a nonlinear response regime. This additional information can include the thickness of the sample and internal stresses in the sample that would occur in the static state. This additional information has value in its own right but some of these can also help improve the accuracy of the measurement of Young's modulus.

In one embodiment, the invention provides an apparatus for measuring elastic properties of a material and including a stimulating energy source coupled to the material to excite the material into vibration and a vibration sensor that can measure movement of the material to provide an electrical signal measuring vibration of the material. A controller executes a stored program to control the stimulating energy source and vibration sensor to: (a) excite the material with the stimulating energy source into linear and nonlinear vibrations; (b) cease excitation of the material to measure the linear and nonlinear vibration with the vibration sensor during a free vibration period; (c) extract a value of Young's modulus from the measured linear vibration; and (d) extract at least one of a thickness of the material and an internal static stress of the material from the measured nonlinear vibration.

It is thus a feature of at least one embodiment of the invention to induce nonlinear vibration measurements to obtain a more complete and more accurate understanding of the elastic properties of the material and/or geometry of the material without the need for separate test hardware.

The apparatus may include a rigid sample holder defining a cylindrical volume aligned with the axis and holding the material in disk form.

It is thus a feature of at least one embodiment of the invention to provide a sample holder consistent with standard designs used in tissue engineering and which precisely establishes boundary conditions of vibration.

The controller may operate to first identify natural resonant frequencies of the material and then to control the stimulating energy source to provide a narrowband excitation of the material at the natural resonant frequencies.

It is thus a feature of at least one embodiment of the invention to allow high signal-to-noise ratio extraction of free vibration in isolated different resonant modes.

The controller may repeat the measurements to provide an output indicating an evolution of at least one of Young's modulus, thickness of the material, and internal static stress of the material over time.

It is thus a feature of at least one embodiment of the invention to allow simultaneous measurement of each of these parameters in repeated single measurements of free vibration decay to provide a simple method of monitoring a material over time, without the need to remove or modify the material in between measurements.

These particular objects and advantages may apply to only some embodiments falling within the claims and thus do not define the scope of the invention.

DETAILED DESCRIPTION OF THE PREFERRED EMBODIMENT

Figure 1:
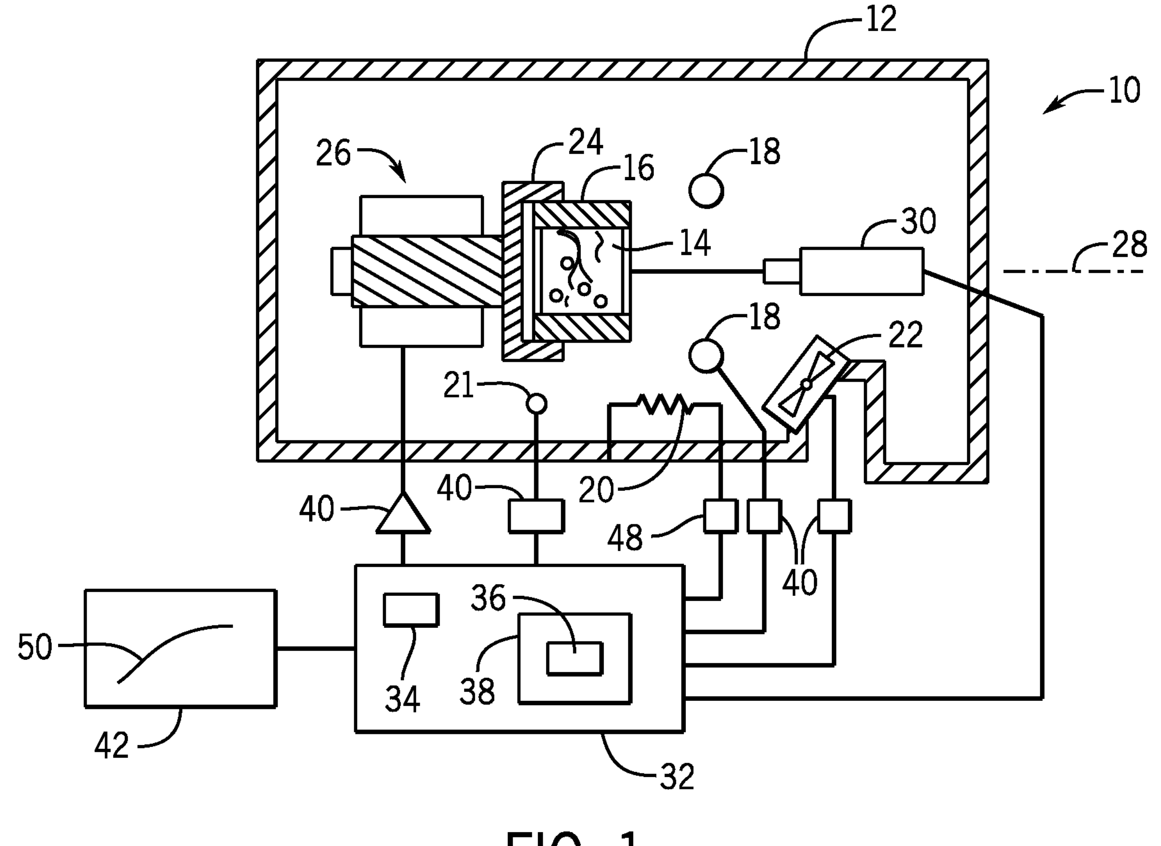
FIG. 1 is simplified depiction of an apparatus constructed according to the present invention showing a sample in a sample holder held in a controlled environment and mounted on an actuator for vibration of the sample and for monitoring vibration of the sample by a vibration sensor as coordinated by a controller executing an operating program.

Referring now to FIG. 1, an apparatus 10 for measuring elastic properties of a material according to the present invention may provide for a housing 12 offering a controlled environment for an elastic sample material 14 retained in a sample holder 16. The material 14 may be a soft and possibly a multiphasic material, for example, with a Young's modulus from 1 Pa to 1 MPa.

The housing 12 may hold one or more material stressors including, for example, ultraviolet lamps 18 that may operate to degrade the elastic material 14, a heater 20 and thermal sensor 21 that may control the temperature to which the material 14 is exposed, and a fan 22 or similar gas introduction port, for example, allowing for the introduction of dry air or other gases to the chamber which may affect the properties of the material 14 over time.

In one embodiment, the sample holder 16 is releasably retained by a chuck 24 attached to a shaker 26, the latter, for example, having an electrodynamic actuator employing a permanent field magnet and coil for controllably shaking the sample holder 16 along a transverse axis 28 according to a received electrical signal. A shaker 26 suitable for this purpose is commercially available from Bruel & Kjaer under the trade designator Type 4810 and provides a frequency range from 0-18 kHz and maximum peak-to-peak displacement of 4 mm (0.16 in) delivering sine forces along an axis 28 up to 10 N (2.25 lbf).

Positioned across from the material 14 on the opposite side of the shaker 26 along the axis 28 is a laser vibrometer 30 directed so as to measure transverse motion of an exposed center point of the material 14 and to produce an electrical signal indicating a velocity of the material 14 at the center point during and after the shaking process. A laser vibrometer 30 suitable for use with the present invention is commercially available as manufactured by Polytec, Inc. under the trade designator PSV-400, and provides up to 40 kHz sampling rates and velocities up to 20 m/s.

Figure 3:
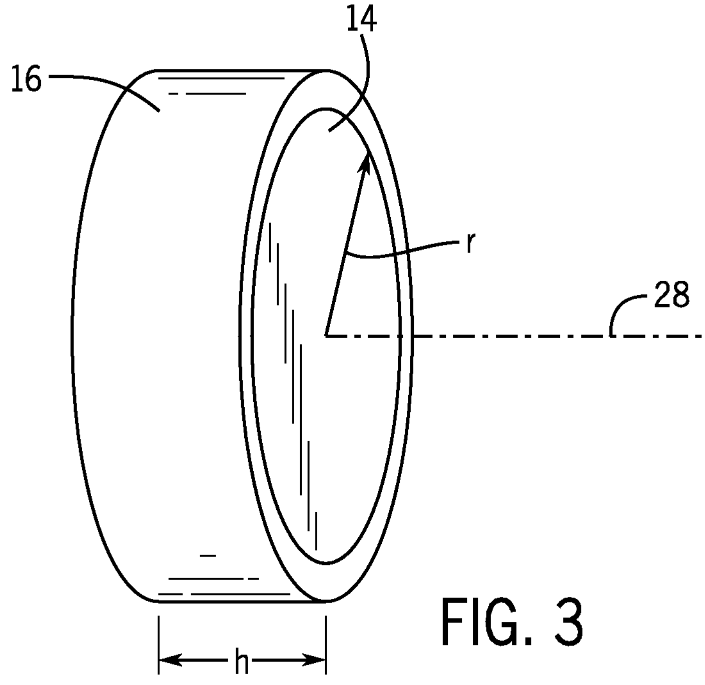
FIG. 3 is a perspective view of a sample holder of FIG. 1 showing various dimensions referred to in the present application.

Referring momentarily to FIG. 3, the sample holder 16 mentioned above, in this regard, may be in the form of a stiff, tubular ring whose axis of symmetry is aligned and centered on axis 28. The sample holder 16 defines a cylindrical internal volume which holds the sample material 14 as a cylindrical disk at its periphery with its faces free to move in vibration without constraint. The material 14 may have a dimension h along the axis 28 and a radius r about a midpoint centered within the sample holder 16 and aligned with the axis 28 and being a point of measurement of the vibrometer 30.

Generally, the material of the sample holder 16 will be much stiffer (at least 10 times or at least 100 times or at least 1000 times) than the material 14 being tested so as to create a rigid boundary with respect to vibrations.

An electronic controller 32 coordinates operation of the shaker 26, the fan 22, the heater 20, and the lamps 18 based on received signals from the vibrometer 30 and the thermal sensor 21 by means of one or more processors 34 executing stored programs 36 held in computer memory 38. According to the operation of that program 36, electrical signals are interchanged with the other components of the apparatus 10 via interface circuitry 40.

The electronic controller 32 may also communicate with a terminal 42 providing for the output of data as will be described below, for example, providing a plot line 50 of changed material properties over time. The terminal 42 may also operate to receive data for control of the apparatus 10 as will be discussed below.

Figure 2:
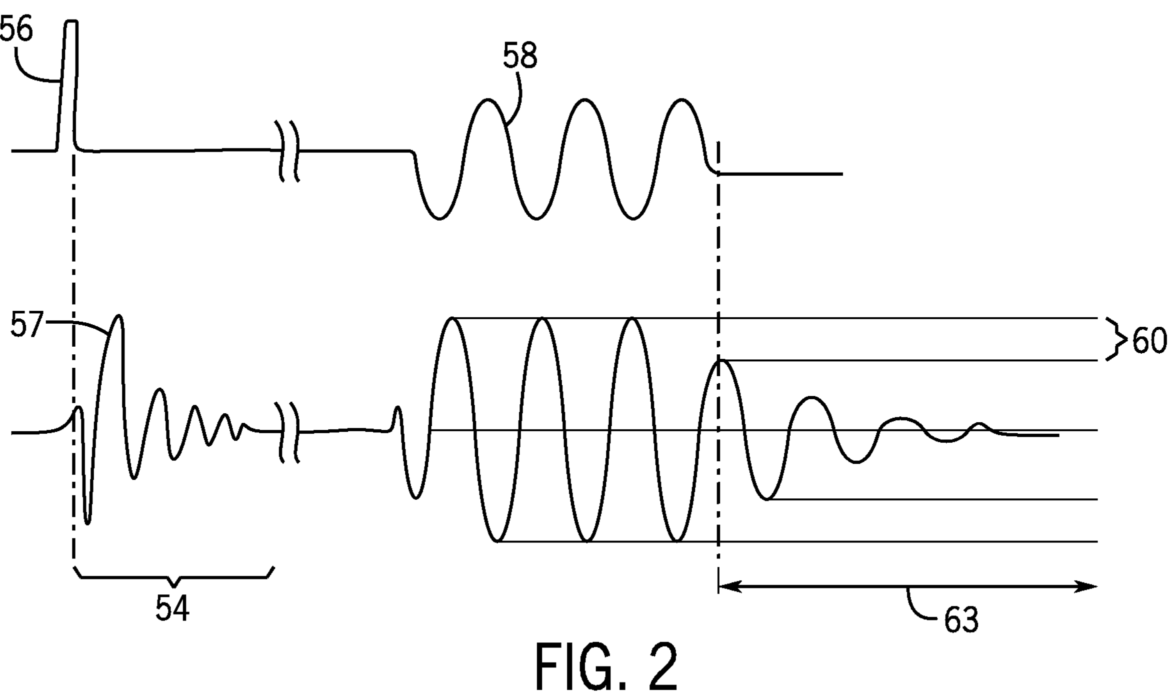
FIG. 2 is a simplified time-plot of electrical signals provided to the actuator of FIG. 1 and vibration signals received from the vibration sensor of FIG. 1.
Figure 4:
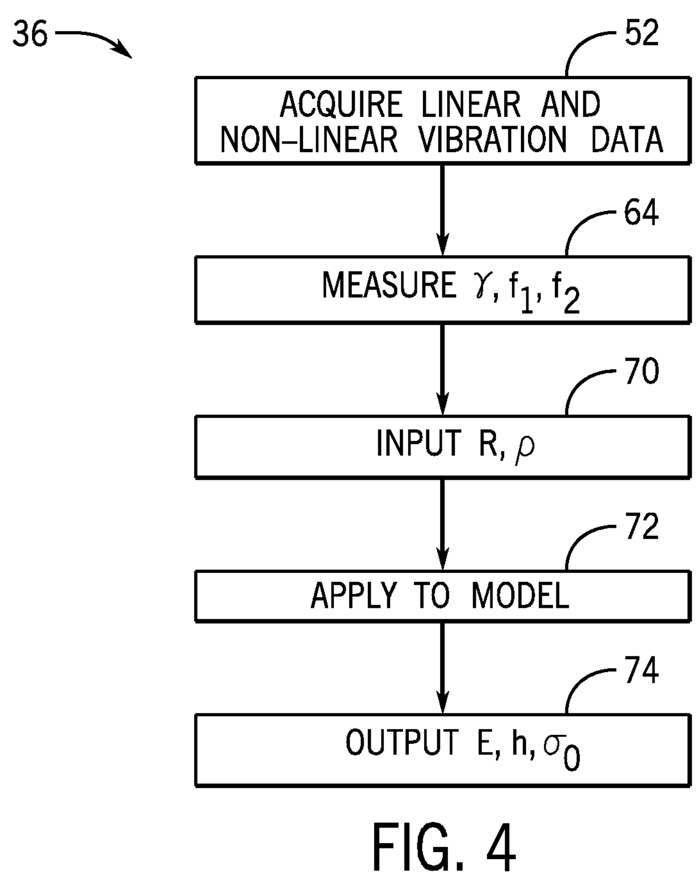
FIG. 4 is a flowchart of the operating program of the controller of FIG. 1.

Referring now to FIGS. 2 and 4, the stored program 36, as indicated by process block 52, controls the apparatus 10 to acquire linear and nonlinear vibration data of the material 14. In a first step in this process, two or more natural modes of resonance of the material 14 (e.g. $f_1$ and $f_2$) as held in the sample holder 16 are identified.

In one embodiment, this determination may be done by applying a broadband sine pulse 56 to the shaker 26 during an interval 54 on the sample holder 16 and hence to excite the material 14 over a broad range of frequencies. A subsequent free vibration 57 of the material as detected by vibrometer 30 is then spectrally analyzed by the program 36 to identify one or more peaks representing natural resonant frequencies of the material 14 (e.g. $f_1$, $f_2$).

The laser sensing point (focal point) of the laser vibrometer 30 may be chosen such that it does not coincide with any nodes (zero displacement points) of the selected vibration modes (e.g., first 2-3 modes). In one embodiment, the laser sensing point is placed at the center of the sample to only measure axisymmetric modes.

Following the resonance characterizing step and after interval 54, a sinusoidal pulse 58 at one of the frequencies (e.g. $f_1$) is applied in a short burst to the shaker 26 to excite the material 14 into a nonlinear excitation range 60. Typically, this burst will be larger than depicted, the burst being shortened in the figure for clarity. The nonlinear excitation range 60 can be recognized in distortion of the sine shape of the free vibration signal 63 detected by the vibrometer 30. This nonlinear excitation range 60 results from a stiffening of the material 14 as it deflects beyond the linear deformation range and thus no longer can be approximated by linear strain assumption. More generally the excursions represented in this nonlinear excitation range 60 will be more than one tenth of the thickness h of the sample and more typically more than 70% of the thickness h. The choice of deflection amount will be determined primarily by how long one is willing to collect vibration measurements to achieve a desired signal-to-noise ratio, with smaller percentage deflections requiring a longer measurement time. When there are only small nonlinearity-induced frequency changes, the necessary high signal-to-noise ratio may be obtained with long sampling times and sensitive equipment such as laser vibrometers. More generally, the proper excitation amount may be determined empirically to match with a given level of signal from the vibrometer.

Once the nonlinear excitation range 60 of nonlinear vibrations is reached, the sinusoidal pulse 58 is terminated to provide a free vibration interval 63 during which the vibration signal from the vibrometer 30 is sampled and stored.

This process is then repeated for at least one second resonant frequency (e.g., $f_2$) to also provide a sample and stored vibration signal.

In accordance with this invention, the inventors have determined that the information contained in free vibration decay 62, including linear and nonlinear regions, provides not only information about elasticity, e.g., Young's modulus (E), but also about the thickness (h) of the material 14 and the internal static stress ($\sigma_0$) of the material 14. The additional information of h allows monitoring of sample thickness, for example, as may change with respect to changes in hydration or the like, and in this respect improves the determination of Young's modulus which is dependent on this thickness. Similarly, the additional information of $\sigma_0$ offers insight into the internal structure of the material 14 and can be important, for example, in predicting the growth and fate of engineered tissues, and also improves the accuracy of the determination of Young's modulus.

A theoretical basis for the inventor's insight can be reached by examining a model of the vibration of a plate discussed in Lien-Wen Chen and Ji-Liang Doong, Vibrations of an Initially Stressed Transversely Isotropic Circular Thick Plate, International Journal of Mechanical Sciences, 26(4): 253-263, 1984, hereby incorporated by reference.

This model describes transverse vibrations (along axis 28) of a prestressed circular plate as follows:

$$(D^*+N_0)\left(\frac{\partial^2 u_0}{\partial r^2}+\frac{1}{r}\frac{\partial u_0}{\partial r}-\frac{u_0}{r^2}\right)+D^*L\left[\frac{1-v}{2r}\left(\frac{\partial w}{\partial r}\right)^2+\frac{\partial w}{\partial r}\frac{\partial^2 w}{\partial r^2}\right]=0 \quad (1)$$

$$Gh\kappa\left(\frac{\partial^2 w}{\partial r^2}+\frac{1}{r}\frac{\partial w}{\partial r}+\frac{\partial \psi}{\partial r}+\frac{\psi}{r}\right)+N_0\left(\frac{\partial^2 w}{\partial r^2}+\frac{1}{r}\frac{\partial w}{\partial r}\right)+ D^*L\left[\frac{v}{r}u_0\frac{\partial^2 w}{\partial r^2}+\frac{\partial u_0}{\partial r}\frac{\partial^2 w}{\partial r^2}+\frac{3}{2}\left(\frac{\partial w}{\partial r}\right)^2\frac{\partial^2 w}{\partial r^2}+\frac{1-v}{r}\frac{\partial u_0}{\partial r}\frac{\partial w}{\partial r}+\frac{\partial^2 u_0}{\partial r^2}\frac{\partial w}{\partial r}+\frac{1}{2r}\left(\frac{\partial w}{\partial r}\right)^3\right]=\rho h\ddot{w} \quad (2)$$

$$(D+M_0)\left(\frac{\partial^2 \psi}{\partial r^2}+\frac{1}{r}\frac{\partial \psi}{\partial r}-\frac{\psi}{r^2}\right)-Gh\kappa\left(\frac{\partial w}{\partial r}+\psi\right)=\frac{\rho h^3}{12}\ddot{\psi} \quad (3)$$

where the superscript (*) represents time derivatives, r is the radial coordinate (shown in FIG. 3), G is the shear modulus, D and D* describe the bending rigidity of the plate, No is a stress resultant, $M_0$ is a bending moment resultant, h is the thickness of the plate (shown in FIG. 3) at a given water loss state, k is the shear correction factor, w(r, t) is the transverse deflection with respect to the center of the mid-plane of the undeformed plate (along axis 28), $u_0$(r, t) is the in-plane displacement, ψ(r, t) is the rotation of cross-section of the plate, v is Poisson's ratio, and L is a variable having a value of zero or one and is used to select different portions of the equation as discussed below.

In this formulation, it will be understood that G is related to Young's modulus, D and D* are related to Young's modulus, Poisson's ratio and thickness, and $N_0$ and $M_0$ relate to internal stress and thickness, demonstrating the necessary functional relationship in the free vibration signal 62 and these desired parameters.

Setting L=1 in equations (1)-(3) and solving them with clamped boundary conditions gives the expression of backbone of the nonlinear vibration. This backbone can be determined from the collected and stored data of the free vibration signal 62, for example, by using the Hilbert transform. The ratio between the coefficients of the backbone, γ, depend on the thickness h, radius R, density ρ, Young's modulus E and internal stress $\sigma_0$ of the disk as:

$$\gamma = g_1(h, R, \rho, E, \sigma_0) \quad (4)$$

Setting L=0 in equations (1)-(3) reduces the system to a linear relationship, and solving them with clamped boundary conditions reveals that linear frequencies of the first two axisymmetric vibration modes, $f_1$ and $f_2$ (for example, as determined at process block 52), are determined by also h, R, ρ, E and $\sigma_0$ of the disk through a series of calculation as:

$$f_1 = G_1(h, R, \rho, E, \sigma_0), \quad f_2 = G_2(h, R, \rho, E, \sigma_0) \quad (5)$$

Together, equations (4) and (5) indicate that it is possible to predict the three unknown parameters h, E and $\sigma_0$ based on measurements of γ, $f_1$ and $f_2$ extracted from the free vibration signal 62 (of FIG. 2) per process block 64 of FIG. 4 after manual inputting of values of R (the maximum value of r shown in FIG. 3) and measure of density ρ per process block 70.

This insight about the information contained in the free vibration interval 63 permits data extracted during the free vibration interval 63 to be processed by numerical methods, for example, developed using a series of experiments of known materials, or by machine learning techniques using a training set from experiments of known materials per process block 72.

These values of h, E and $\sigma_0$ can be output per process block 74, for example, numerically or in a graphic form over time with process blocks 52, 64, 70, and 72 being repeated appropriately.

Figure 5:
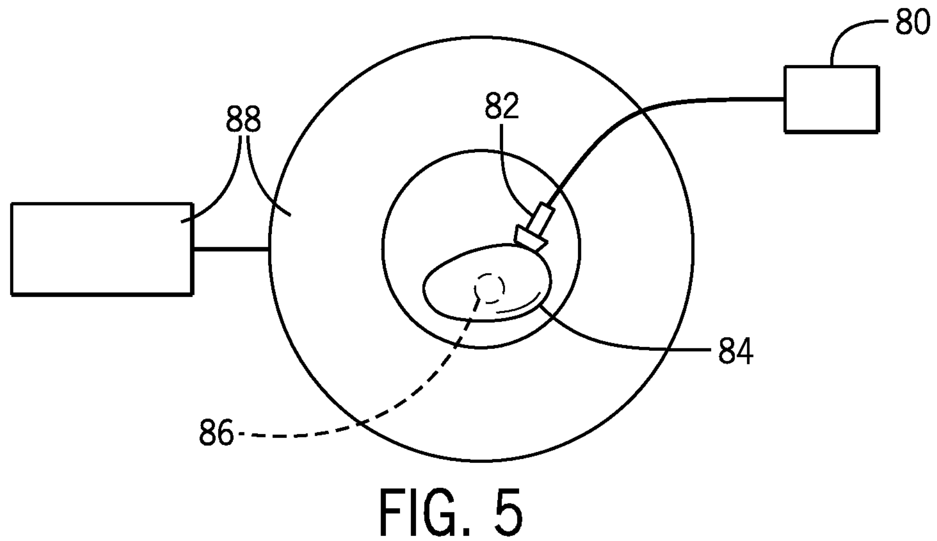
FIG. 5 is a schematic representation of an alternative embodiment of the apparatus useful in medical applications.

Referring now to FIG. 5, the present technique can be used not only for laboratory or high throughput industrial testing but also for medical imaging. In this latter case, for example, an ultrasound system 80 and ultrasound probe 82 as applied to tissue of a patient 84 may be used to produce a desired vibration of tissue being investigated in a region of interest 86, for example, employing acoustic radiation force (ARF) techniques thus fulfilling the function of the shaker 26. Measurement of the vibration of this tissue per the function of the laser vibrometer 30 may be implemented, for example, by an MRI machine 88 monitoring tissue motion, for example, using magnetic resonance elastography.

A variety of different elements may be used to implement the function of the shaker 26 including acoustic transducers coupled to the material 14 through the air such as speakers or the like, jets of air impinging on the material 14, and mechanically contacting transducers such as those using piezoelectric elements, motors, or the like. Similarly, vibration measurement may be obtained not only through a laser vibrometer 30 but through other contact and non-contact techniques including ultrasound, imaging, surface contact accelerometers, capacitive sensors, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The term "narrowband" relates to a signal with a full width half maximum of less than 20% of the center wavelength value and typically less than 10% of the center wavelength value and in some cases less than 6% of the center wavelength value. Measure of elasticities should be understood to include a family of measurements which indicate a relationship between stress and strain or those which have a monotonic functional relationship with Young's modulus allowing them to substitute for Young's modulus.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a computer" or the like can be understood to include one or more such devices that can communicate in a stand-alone and/or a distributed environment(s) or an Internet connection to such a device individually or jointly executing the stored program. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for measuring elastic properties of a material comprising:

a stimulating energy source coupled to the material to excite the material into vibration;

a vibration sensor adapted to provide an electrical signal measuring vibration of the material; and a controller executing a stored program to control the stimulating energy source and vibration sensor to:

(a) excite the material with the stimulating energy source into linear and nonlinear vibration;

(b) cease excitation of the material to measure the linear and nonlinear vibration with the vibration sensor during a free vibration period;

(c) extract a value of elasticity from the measured linear vibration; and (d) extract at least one of a thickness of the material and an internal static stress of the material from the measured nonlinear vibration.

2. The apparatus of claim 1 wherein the stimulating energy source provides a dominant vibration of material along an axis and the thickness is along the axis.

3. The apparatus of claim 2 wherein the controller excites the material with the stimulating energy source to an amplitude at least one tenth of a thickness of the material along the axis.

4. The apparatus of claim 2 further including a rigid sample holder defining a cylindrical volume aligned with the axis and holding the material in disk form.

5. The apparatus of claim 1 wherein the stimulating energy source is an electromechanical actuator coupled to the material.

6. The apparatus of claim 1 wherein the vibration sensor is a noncontact vibration sensor.

7. The apparatus of claim 1 wherein the vibration sensor is a laser vibrometer.

8. The apparatus of claim 1 wherein the controller further receives an input indicating a density of the material.

9. The apparatus of claim 1 wherein the controller further receives a dimension of the material perpendicular to an axis of vibration.

10. An apparatus for measuring elastic properties of a material comprising:

a stimulating energy source coupled to the material to excite the material into vibration;

a vibration sensor adapted to provide an electrical signal measuring vibration of the material; and a controller executing a stored program to control the stimulating energy source and vibration sensor to:

(a) excite the material with the stimulating energy source into linear and nonlinear vibration;

(b) cease excitation of the material to measure the linear and nonlinear vibration with the vibration sensor during a free vibration period;

(c) extract a value of elasticity from the measured linear vibration; and (d) extract at least one of a thickness of the material and an internal static stress of the material from the measured nonlinear vibration; and wherein (a) includes an initial operation of identifying a at least one resonant frequency of the material and the controller operates the stimulating energy source to provide a narrowband excitation of the material specific to the identified at least one resonant frequency.

11. The apparatus of claim 10 wherein the initial operation identifies the natural resonant frequency of material by applying a broadband impulse force to the material with the stimulating energy source and analyzing a spectrum of the vibrations received by the vibration sensor.

12. The apparatus of claim 1 wherein (d) extracts thickness of the material and not internal static stress.

13. The apparatus of claim 1 wherein (d) extracts internal static stress and not thickness of the material.

14. The apparatus of claim 1 further including (e) of repeating (a)-(d) to provide composite values of elasticity and at least one of thickness of the material and the internal static stress of the material combining individual measurements.

15. The apparatus of claim 1 further repeating (e) to provide an output indicating an evolution of at least one of elasticity, thickness of the material, and internal static stress of the material over time.

16. The apparatus of claim 1 further including at least one of a lamp, a heater, and a fan controllable by the controller to provide an environmental stress to the material from illumination, heating, or dehydration.

17. The apparatus of claim 1 wherein the material has a Young's modulus between 1 Pa and 1 MPa.

18. The apparatus of claim 1 wherein the measure of elasticity is Young's modulus.

19. A method of measuring elastic properties of a material employing an apparatus providing:

a stimulating energy source coupled to the material to excite the material into vibration;

a vibration sensor adapted to provide an electrical signal measuring vibration of the material; and a controller executing a stored program to control the stimulating energy source and vibration sensor; the method comprising operating the controller to:

(a) excite the material with the stimulating energy source into linear and nonlinear vibration;

(b) cease excitation of the material to measure the linear and nonlinear vibration with the vibration sensor during a free vibration period;

(c) extract a value of Young's modulus from the measured linear vibration; and (d) extract at least one of a thickness of the material and an internal static stress of the material from the measured nonlinear vibration.

* * * * *